United States Patent [19]

Antrim

[11] Patent Number: 5,180,669
[45] Date of Patent: Jan. 19, 1993

[54] LIQUEFACTION OF GRANULAR-STARCH SLURRIES USING ALPHA-AMYLASE IN THE PRESENCE OF CARBONATE ION

[75] Inventor: Richard L. Antrim, Hawthorne Woods, Ill.

[73] Assignee: Genencor International, Inc., Rochester, N.Y.

[21] Appl. No.: 676,770

[22] Filed: Mar. 27, 1991

[51] Int. Cl.$^5$ .............. C12P 19/14; C12P 19/12; C12N 1/00

[52] U.S. Cl. .................... 435/99; 435/100; 435/836

[58] Field of Search ............ 435/836, 99, 100

[56] References Cited

U.S. PATENT DOCUMENTS 4,376,824  3/1983  Hurst et al. .................. 435/94
4,774,183  9/1988  Fan ............................. 435/94

Primary Examiner—David M. Naff
Assistant Examiner—Deborah K. Ware

[57] ABSTRACT

A starch slurry is liquified with alpha-amylase to produce fructose by a process wherein carbonate ion in excess of an amount needed to adjust the pH to about 5.0 to 6.0 is added to the slurry and the pH of the slurry is adjusted to about 5.0 to 6.0. The excess amount is preferably about 2 mM to 20 mM. This process enables obtaining consistent and complete liquefaction.

8 Claims, No Drawings

LIQUEFACTION OF GRANULAR-STARCH SLURRIES USING ALPHA-AMYLASE IN THE PRESENCE OF CARBONATE ION

FIELD OF THE INVENTION

The present invention relates to the liquefaction of grain starch in the production of dextrose, fructose, alcohol and the like at pH's less than 6 using alpha amylase. It also relates to the addition of carbonate ion to the process to reduce liquefaction time and consistently achieve adequate liquefaction.

BACKGROUND INFORMATION

Grains such as corn have long been used as a source of starch. One of the classic methods of separating the starch and then using it in other industrial processes is the wet-milling process. This method is a highly specific and integrated system developed to separate the major components of a grain kernel as completely as possible (see Stanley A. Watson, *Starch: Chemistry & Technology*, Vol. II, *Industrial Aspects*, Academic press, New York, 1967, pp 30-51). A final granular starch slurry coming out of the wet milling process can be used in a variety of industrial processes. One of the most important processes is the conversion of starch to high fructose syrup. In practice, this conversion involves four major steps; namely liquefaction of granular starch slurry, saccharification of the liquified starch into dextrose, purification, and then isomerization of dextrose into fructose. The most popular grain used in this process is corn in the production of high fructose corn syrup (See N. H. Asehengreen, et al, Vol. 31, pp 64-66 (1979)). During the four step conversion to fructose, the granular starch slurry is varied wildly in pH. The pH of the slurry coming out of the commercial wet-milling operation is about 4 then raised to a pH of from 6-6.4, and calcium is added. For saccharification of the starch the pH is lowered to 4.3-4.5 and for the final isomerization the pH is increased back to about 7.8. The result of these wide shifts in pH is a high ion exchange requirement to desalt the syrup during and after processing. Furthermore, high pH causes byproduct formation, sugar breakdown, color formation, and an overall decrease in product yield. The factors add millions of dollars annually to the cost of high fructose syrup production. The industrial isomerization process is currently very efficient due to current processing techniques and the short processing time. Accordingly, it would be useful if the liquefaction step could be carried out at lower pH's. It is possible to perform liquefaction at pH's less than 6 (see e.g. U.S. Pat. No. 4,376,824); however, the liquefaction is sometimes unexplainably incomplete.

SUMMARY OF THE INVENTION

The present invention overcomes the difficulties of the prior art. Namely, a lower pH method of consistently liquefying granular starch slurry comprising:
a) Adjusting the pH of a granular starch slurry to from about 5.0 to 6.0;
b) adding from about 12 liquefons alpha amylase per gram of starch in the slurry;
c) adding a carbonate ion in excess of the amount needed to buffer the solution;
d) reacting the slurry for the appropriate time and temperature to liquefy the starch.

DETAILED DESCRIPTION OF THE INVENTION

It has been discovered that when alpha amylase is added to a granular starch slurry at pH's less than 6 a satisfactory liquefaction can be achieved. As used herein "granular starch slurry" refers to any of the various edible grains which have been wet milled to produce a starch slurry. Examples of edible starch containing grains include corn, wheat, milo and the like. Typically, the dry starch component is roughly between about 30% and 40% on a weight basis of the slurry with the examples herein adjusted to 35% starch.

The enzyme used herein for addition to the slurry is alpha amylase. Alpha amylase is an endo-amylolytic enzyme capable of promoting random cleavage of $\alpha$-1,4 glucosidic bonds within the starch molecule and is produced by a number of types of microorganisms such as members of Bacillus and Aspergillus. Especially preferred are alpha amylase enzymes derived from *Bacillus licheniformis* and *B. subtilis*. Enzyme activity is measured in a unit called the liquefon. In the practice of the invention, at least about 10 liquefons of alpha amylase activity are used per dry gram of starch present in the slurry. Typically the amount is from about 10-20 liquefons/g, preferably 12-14 liquefons/g, although where a faster result is desired, more alpha amylase may be added.

The liquefaction may be carried out in a one-stage or conventional two-stage process. In a two-stage process alpha amylase is added to a slurry, and the slurry is first held at 100°-105° C. for a period of about 2-10 minutes. Next, the temperature is reduced to about 90°-100° C. and held up to 120 minutes, preferably no greater than 90 minutes.

Starch liquefaction processes are generally carried out in the presence of calcium to impart heat stability to the enzyme. Various alpha amylases have differing heat stabilities and so somewhere between 20 ppm and 200 ppm is added. Calcium in the form of lime has frequently been used for this purpose wherein it also serves to help adjust pH levels upward from the initial low pH of the fresh starch slurry. In general it is desirable that calcium levels be under 100 ppm, due in part to incompatibility with the downstream isomerization process.

The present invention maintains the reaction at a pH of about 6 or lower down to about 5.0 during liquefaction. The preferred pH is as close to 5.0 as possible. Calcium compounds, e.g. lime or calcium carbonate, are commonly used to adjust the pH upward from the initial pH of the granular starch during liquefaction. Other compounds used to adjust the pH upward include sodium hydroxide and sodium carbonate.

In the practice of the invention a key unobvious and novel aspect of the liquefaction process taught herein is the addition of carbonate ion in excess of what is necessary to adjust the pH. As mentioned above, normally enough carbonate is added to adjust the pH up from 4 to the desired pH. However, the applicant has found that an excess of available carbonate allows complete liquefaction in reasonable periods of time at lower pH values compared with those processes without carbonate excess. Since extra carbonate would tend to increase the pH of the slurry beyond the desired 5-6 pH range, the excess carbonate is usually neutralized with a source of hydrogen ion usually an inorganic acid such as hydrochloric or sulfuric acid. Carbonate may be added, for example, as sodium bicarbonate, sodium carbonate, or as carbon dioxide. In general, the concentration of carbonate in excess of what is necessary would be 10 mM preferably 2 mM to 20 mM.

The result of using the process herein in the presence of excess carbonate is that we gain two-fold, namely, the process can be carried out at a lower pH than would otherwise be possible. Further, the resultant slurry will have little or no raw starch remaining with a Dextrose Equivalent (DE) of about 10 or less.

The following examples are representative of the invention. One skilled in the art would be able to substitute conditions, temperatures, enzymes, carbonate ions and the like and are intended only as instructive as well as representative of best mode.

EXAMPLE 1

Alpha Amylase Activity Determination

The sample illustrates a method for the determination of alpha-amylase activity.

The determination of alpha-amylase activity is based upon the ability of native starch to form a blue colored complex with iodine, and the disappearance of this color when starch is hydrolyzed into shorter dextrin molecules. The alpha amylase activity was defined in terms of the digestion time required to produce a color change denoting a definite state of dextrination of the starch.

REAGENTS

Phosphate buffer-Sodium hydroxide (25.3 g) and potassium dihydrogen phosphate (340 g) were dissolved in water and diluted to approximately 2 liters. The buffer was cooled to room temperature and the pH adjusted to 6.2±0.1. The buffer was diluted to 2 liters in a volumetric flask.

Starch substrate-Ten grams (dry substance) of soluble Lintner Starch were suspended in 50 ml of water and washed into approximately 300 ml of boiling water. The suspension was again brought to boiling and boiled for 5 minutes with constant stirring. The starch solution was cooled with constant stirring to room temperature and 125 ml of phosphate buffer were added. The solution was diluted to 500 ml with water. The starch substrate was made fresh daily.

Stock iodine solution-Iodine crystals (5.5 g) and potassium iodide (11.0 g) were dissolved in water and volumetrically diluted to 250 ml. The solution was kept from light and was prepared monthly.

Dilute iodine solution-Potassium iodide (20 g) and 2 ml of stock iodine solution were dissolved in water and diluted volumetrically to 500 ml. The solution was made fresh daily.

Enzyme diluting solution-Calcium chloride (11.1 g) was dissolved in 4 liters of water.

Water used for all reagents was either distilled or deionized.

APPARATUS

Constant temperature bath set at 30° C.±0.2° C. Hellige comparator equipped with a special alpha amylase color disc (catalog number 620-S5). Precision bore 13 mm square tubes from Hellige Inc. One and five milliliter automatic pipets.

PROCEDURE

The unknown alpha amylase sample was diluted to 10-15 LU/ml (as defined below) with the enzyme diluting solution. For many commercial alpha amylase preparations a suitable dilution was found to be 2000.

Five milliliter aliquots of dilute iodine solution were dispensed into 13×100 mm test tubes and 10 ml of starch solution was placed in a 23×200 test tube and all tubes were attemperated in the 30° C. water bath.

Five milliliters of diluted enzyme solution (also at 30° C.) were mixed with the starch solution and timing was begun. At appropriate time intervals, 1 ml aliquots of the hydrolyzing mixture were transferred to a test tube containing the attemperated dilute iodine solution. The starch-iodine solution was mixed and transferred to a 13 mm precision tube and the color was compared with the standard alpha amylase color disc in the Hellige comparator. When the time of the end point was approached, samples were taken at 0.25 minute intervals.

The time required for the colors of the samples and the color disc to match were recorded and the activity in Liquefons per gram or ml was calculated according to the formula:

$$LU/\text{ml or } LU/\text{g} = \frac{570}{V \times t} \times D$$

Where
LU = liquefon unit
V = volume of sample (5 ml)
t = dextrinization time (minutes)
D = dilution factor = dilution volume/ml or g of added enzyme.

EXAMPLE 2

Starch Liquefaction Conditions. Determination of Liquefied Starch DE

This sample describes the process for the liquefaction of starch using a jet cooker.

Starch liquefaction was typically performed using a Hydroheater M 103-M steam jet equipped with a 2.5 liter delay coil behind the mixing chamber and a terminal back pressure valve. Starch was fed to the jet by a Moyno pump and steam was supplied by a 150 psi steam line, reduced to 90–100 psi. Temperature probes were installed just after the Hydroheater jet and just before the back pressure valve.

Starch slurry was typically obtained fresh daily from a corn wet miller and used the same day. The starch was diluted to the desired solids level with deionized water and the pH of the starch was adjusted with 2% NaOH or saturated $Na_2CO_3$. Typical liquefaction conditions were:

| Starch | 32%–35% solids |
| Calcium | 35–45 ppm (25 ppm added) |
| pH | 5.0–6.0 |
| Alpha amylase | 12–14 LU/g starch dry basis |

Starch was introduced into the jet at about 500 ml/min. The jet temperature was held at 103° C.–105° C. Samples of starch were transferred from the jet cooker to a 95° C. second stage liquefaction bath and held for 90 minutes.

The degree of starch liquefaction was measured immediately after the second stage liquefaction by determining the dextrose equivalence (DE) of the sample and by testing for the presence of raw starch, both according to the methods described in the *Standard Analytical Methods of the Member Companies of the Corn Refiners Association, Inc.*, sixth edition. Starch, when treated generally under the conditions given above and at pH 6.0, will yield a liquefied starch with a DE of about 10 and with no raw starch.

EXAMPLE 3

Effect of pH on Starch Liquefaction by Alpha Amylase

This example illustrates that the ability of alpha amylase to liquefy starch is a function of pH.

Fresh starch slurry was liquefied as described in example 2 using 13.2 LU/g starch and between pH 5.2 and 6.0. As shown in Table I, as the pH was decreased, the DE of the liquefied starch also dropped. Thus, alpha amylase liquefied starch best at about pH 6.0 and as the pH decreased the degree of starch liquefaction (as measured by DE) lessened.

TABLE I

Effect of pH on Starch Liquefaction

| Reaction pH | | | Raw |
|---|---|---|---|
| Jet Inlet | Jet Outlet | 90 min DE | Starch |
| 6.0 | 6.0 | 11.4 | — |
| 5.7 | 5.7 | 10.0 | — |
| 5.4 | 5.5 | 7.7 | + |
| 5.2 | 5.3 | 1.3 | + |

Table I also shows the effect of liquefaction upon the pH of the starch slurry. The exit pH of liquefied starch is not normally measured by corn wet millers. Any change in pH is believed to be small. In these experiments the change in pH caused by liquefaction was 0.0 to 0.1 pH unit.

EXAMPLE 4

Effect of Carbonate Ion on Starch Liquefaction at Low pH

This example illustrates effect of carbonate ion on the ability of alpha amylase to liquefy starch at pH lower than 6.0.

Carbonate ion (as $Na_2CO_3$) was added to starch slurry to provide concentrations ranging from 3.5 to 10.5 mm and the pH of the slurries adjusted to the desired pH with 6% HCl. The starch slurries were liquefied as described in Example 2 using an alpha amylase concentration of 13.2 LU/g starch. The initial pH of the starch was varied from 4.8 to 5.7.

Table II shows the effect of added carbonate upon starch liquefaction. The addition of carbonate increased the shift seen in the pH of the starch as it was liquefied (inlet vs exit pH on the liquefaction jet). Depending upon the concentration of the added carbonate the pH shifted upward (toward pH 7) by as much as 0.5 pH unit.

Because pH affects the ability of alpha amylase to liquefy starch, it is important to note this pH shift. However, the improvement seen in starch liquefaction with the addition of carbonate is over and above that which would be expected by the pH shift alone. To facilitate the comparison of data generated in the presence or absence of carbonate, all tables contain both the initial and final pH values of the liquefaction while data of the figures are based only on the final pH values of the starch liquefaction. This presentation will clearly show that the improvement in liquefaction at low pH values caused by the addition of carbonate is greater than that caused by the pH shift alone.

TABLE II

The Effect of Carbonate on Starch Liquefaction by Alpha Amylase

| | pH | | | Raw Starch |
|---|---|---|---|---|
| Conc. | Initial | Final | 90 min DE | test |
| 0.0 Mm | 6.0 | 6.0 | 11.3 | — |
| 3.5 mM | 5.7 | 6.0 | 13.1 | — |
| 0.0 mM | 5.7 | 5.7 | 10.0 | + |
| 3.5 mM | 5.4 | 5.6 | 10.9 | — |
| 0.0 mM | 5.4 | 5.5 | 7.7 | + |
| 5.0 mM | 5.2 | 5.5 | 10.3 | — |
| 7.0 mM | 5.1 | 5.4 | 9.7 | — |
| 0.0 mM | 5.2 | 5.2 | 1.3 | + |
| 7.0 mM | 5.0 | 5.1 | 2.8 | + |
| 10.5 mM | 5.0 | 5.2 | 6.5 | + |

As Table II shows, when starch treated with added carbonate was liquefied at a pH several tenths below that of untreated starch and the final pH was the same or slightly lower than for untreated starch, the degree of liquefaction as measured by DE is significantly greater.

EXAMPLE 5

The Effect of pH and Carbonate on Starch Liquefaction of Starch from a Separate Source This example illustrates that the effect of pH and carbonate on the liquefaction of starch by alpha amylase is a general phenomenon in that the effect can be demonstrated with a starch from a different corn wet milling plant.

Starch slurry was obtained from a second corn wet milling plant and liquefied as generally described in Example 2 at pH 5.9, 5.6 and 5.3. The starch was then liquefied at pH 5.2 in the presence of 10 mM carbonate. Table III summarizes the results of these experiments.

TABLE III

The Effect of pH and Carbonate on Starch Liquefaction

| | pH | | |
|---|---|---|---|
| conc. | Initial | Final | 90 min DE |
| 0.0 mM | 5.9 | 6.2 | 9.8 |
| | 5.6 | 5.8 | 6.8 |
| | 5.3 | 5.4 | 1.7 |
| 10.0 mM | 5.2 | 5.6 | 7.7 |

As shown in Table III, as the pH of the starch slurry was decreased, the degree of liquefaction of the starch also decreased. However, when 10 mM carbonate was added to the starch before liquefaction, a 75% increase in the DE of the liquefied starch was observed. Again, as in Example 4, the addition of carbonate increased the pH change that occurred when the starch was liquefied. As before, to differentiate between the effect caused by the pH shift and that caused by the added carbonate, only the final pH values were used in the comparisons.

What is claimed is:
1. A process of liquefying a granular starch slurry comprising:
   (1)
   a) adding to the slurry an excess of carbonate ion in an amount of from about 2 mM to about 20 mM in excess of the amount of carbonate ion needed to adjust the pH of the slurry to a pH of about 5.0 to about 6.0 and adjusting the pH of the slurry to a pH from about 5.0 to about 6.0;

b) adding to the slurry about 10 liquefons or more of an alpha-amylase per gram of dry starch in the slurry; and (2) heating the slurry from step (1) at a temperature from about 100° C. to about 105° C. for an initial period and then holding the slurry at a temperature from about 90° C. to about 100° C. for a length of time sufficient to liquefy the starch.

2. A process according to claim 1 wherein the alpha amylase is derived from *Bacillus lichenformis*.

3. A process according to claim 1 wherein in step (2) the initial period comprises from about 2 minutes to about 10 minutes.

4. A process according to claim 1 wherein the carbonate ion is provided by addition of sodium bicarbonate, sodium carbonate or carbon dioxide.

5. A process according to claim 1 which is performed until the DE of the slurry is about 10 or less.

6. A process of liquefying a granular starch slurry comprising:

(1)
a) adding to the slurry an excess of carbonate ion in an amount of from about 2 mM to about 20 mM in excess of the amount of carbonate ion needed to adjust the pH of the slurry to a pH of about 5.0 to about 6.0 and adjusting the pH of the slurry to a pH from about 5.0 to about 6.0;

b) adding to the slurry from about 10 liquefons to about 14 liquefons of an alpha-amylase per gram of dry starch in the slurry; and (2) heating the slurry from step (1) for an appropriate time and at an appropriate temperature effective to liquefy the starch.

7. A process of claim 6, wherein the alpha-amylase is derived from *Bacillus licheniformis*.

8. A process of claim 6, wherein the slurry is heated in step (2) at a temperature from about 100° C. to about 105° C. for an initial period of from about 2 minutes to about 10 minutes and then holding the slurry at a temperature from about 90° C. to about 100° C. for a period sufficient to liquefy the starch.

* * * * *